United States Patent
Sweeney, II et al.

(10) Patent No.: US 10,413,371 B2
(45) Date of Patent: Sep. 17, 2019

(54) DYNAMIC FEEDBACK END EFFECTOR

(71) Applicant: Rubicon Spine LLC, Sarasota, FL (US)

(72) Inventors: Thomas M. Sweeney, II, Sarasota, FL (US); John D. Kuczynski, Sarasota, FL (US)

(73) Assignee: Rubicon Spine, LLC, Sarasota, FL (US)

( * ) Notice: Subject to any disclaimer, the term of this patent is extended or adjusted under 35 U.S.C. 154(b) by 59 days.

(21) Appl. No.: 15/612,290

(22) Filed: Jun. 2, 2017

(65) Prior Publication Data

US 2017/0348062 A1    Dec. 7, 2017

Related U.S. Application Data

(60) Provisional application No. 62/392,523, filed on Jun. 3, 2016.

(51) Int. Cl.

| | |
|---|---|
| *A61B 17/00* | (2006.01) |
| *A61B 17/16* | (2006.01) |
| *A61B 17/70* | (2006.01) |
| *A61B 34/32* | (2016.01) |
| *A61B 46/10* | (2016.01) |
| *A61B 34/30* | (2016.01) |
| *A61B 90/00* | (2016.01) |

(52) U.S. Cl.
CPC .......... *A61B 34/32* (2016.02); *A61B 17/7082* (2013.01); *A61B 17/7083* (2013.01); *A61B 34/30* (2016.02); *A61B 46/10* (2016.02); *A61B 17/1626* (2013.01); *A61B 17/1671* (2013.01); *A61B 2017/00026* (2013.01); *A61B 2017/00477* (2013.01); *A61B 2090/031* (2016.02); *A61B 2090/064* (2016.02); *A61B 2090/066* (2016.02)

(58) Field of Classification Search
CPC ......... A61B 34/32; A61B 34/30; A61B 46/10; A61B 17/1671; A61B 17/7082; A61B 17/7083; A61B 19/20; A61B 19/5244; A61B 19/5225; A61B 19/2203; A61B 19/50; A61B 2090/031; A61B 2090/064; A61B 2090/066; A61B 2917/00026; A61B 2917/00477; A61B 2019/207; A61B 2019/5255; A61B 2019/5236; A61B 2019/5238; A61B 2019/524; A61B 2019/2211
USPC ............... 600/417, 429, 424; 606/86 A, 130; 901/41, 15, 16; 700/260, 261
See application file for complete search history.

(56) References Cited

U.S. PATENT DOCUMENTS

| | | | |
|---|---|---|---|
| 9,283,048 B2* | 3/2016 | Kostrzewski | .......... A61B 34/30 |
| 2015/0305817 A1* | 10/2015 | Kostrzewski | .......... A61B 34/70 606/130 |
| 2016/0151120 A1* | 6/2016 | Kostrzewski | ...... A61B 17/1671 606/130 |

* cited by examiner

*Primary Examiner* — Pedro Philogene
(74) *Attorney, Agent, or Firm* — Kim IP Law Group PLLC (57) ABSTRACT

An end effector system for use in spinal surgery may be described herein. The end effector comprises a sterile section and a non-sterile section. The sterile section comprises an instrument holder that has pins for piercing a plastic sleeve. The instrument holder holds an instrument for performing spinal surgery. The non-sterile section comprises an end effector. The end effector comprises a motor and a transducer. The motor applies a torsional and axial force to the instrument. The transducer provides feedback to the end effector system to adjust a force applied to the instrument.

20 Claims, 10 Drawing Sheets

DYNAMIC FEEDBACK END EFFECTOR

CROSS-REFERENCE TO RELATED APPLICATIONS

This application claims the benefit of U.S. Provisional Patent Application 62/392,523 filed on Jun. 3, 2016, the contents of which are hereby incorporated by reference.

FIELD OF INVENTION

The present invention is in the field of robotic surgeries.

BACKGROUND

Industrial robots have been in use since the 1960's, with the automobile industry being the first to apply such technology. Later, other industries applied robots to their manufacturing processes, increasing productivity, as well as accuracy and repeatability. Robots have been used for orthopedic surgery since the early 1990's. The ROBODOC system was the first to do the bone resections for joint replacement using a robot with a mill that profiled he surfaces of the bone in the proper shape and orientation to receive prosthesis. Laker MAKO Surgical produced the RIO system which is used to perform partial knee and total hip replacement surgery. Mazor Robotics currently makes the Renaissance robotic surgery system to assist in the performance of spinal surgeries.

In the field of Robotics, the end effector is the device at the end of the robotic arm that interacts with the work environment of the robotic system. Some example of end effectors in industrial robotics are grippers, designed to grab and release an item when the robot is used for pick and place operations, an arc welder, when the robot is used for welding operations, or a spray paint nozzle, when the robot is used for painting operations. In the case of the ROBODOC robot, the end effector is a pistol-shaped pneumatic drill equipped with a milling cutter, used for cutting the proximal tibia.

Robots are currently utilized in spine surgery to provide axial alignment to the pedicles and to control the depth of the tool or implant being inserted into the pedicle. The software utilizes CT data from the patient to help the surgeon plan a surgery in a virtual environment. During the operation, a positioning rack may be attached to the patient's spine and acts as a fixed base. Anteroposterior (AP) and Medio-Lateral (ML) X-rays are used to create a 3-dimensional (3D) alignment of the patient that matches the patient's CT data and used to create a coordinate system (for example, X, Y, X, Yaw, Pitch and Roll) for the robot to use.

SUMMARY

An end effector described herein may be applied to an industrial robotics system that may be used to perform spinal reconstructive surgery. The end effector may have specific capabilities and features that may allow a robotic system to perform surgical steps more effectively and safely. When a robot is performing surgical steps, the end effector may act as the "hands" of a surgeon. The end effector may hold the instrument. The end effector may maneuver the instrument, like a surgeon would, with precision and the appropriate amount of force. The end effector may also detect problems, like the surgeon's hands would, for example, if too much force is encountered during a surgical step. The end effector may also control the force applied to a cutting tool and adjust the feed rate accordingly. A surgical end effector system that moves the instruments to perform a surgical operation and provide force feedback for safety and control of the instrument motion is described herein.

DETAILED DESCRIPTION

This invention is described in the following description with reference to the Figures, in which like reference numbers represent the same or similar elements. While this invention is described in terms of modes for achieving this invention's objectives, it will be appreciated by those skilled in the art that variations may be accomplished in view of these teachings without deviating from the spirit or scope of the present invention. The embodiments and variations of the invention described herein, and/or shown in the drawings, are presented by way of example only and are not limiting as to the scope of the invention.

Unless otherwise specifically stated, individual aspects and components of the invention may be omitted or modified, or may have substituted therefore known equivalents, or as yet unknown substitutes such as may be developed in the future or such as may be found to be acceptable substitutes in the future. The invention may also be modified for a variety of applications while remaining within the spirit and scope of the claimed invention, since the range of potential applications is great, and since it is intended that the present invention be adaptable to many such variations.

In the field of robotics, the end effector or end-of-arm tooling (EOAT) (the terms end effector and EOAT are used interchangeably throughout) may be a device, or devices, attached to the end of a robot arm. The EOAT may allow the robotic system to interact with the environment. The nature of this device may depend on how the EOAT may interact with its environment and the work that needs to be performed by the robotic system. Currently in industrial applications the EOAT may perform a variety of functions.

The EOAT may act like a "hand" of a robotic system; gripping a workpiece that may need to be manipulated or held. This may be accomplished with two or more "fingers" that pinch a workpiece between them, known as impactive gripping. Holding may also be accomplished by means of a vacuum (or an electromagnet), known as astrictive gripping. Ingressive gripping, where pins or some other feature(s) actually penetrate the surface of the object being handled, may be commonly used in the textile industry. Contigutive holding may require direct contact (for example, glue, surface tension, freezing, and the like) and may be used to hold and manipulate low mass objects. The workpiece may also be equipped with a holding feature that engages with the end effector. This may often be done in cases where the workpiece needs to be held accurately and rigidly, such as in the case of a tool or instrument.

The end effector may also be a specific tool or machine for performing a specific job. In many industrial applications, the end effector may be a welding torch that may be used to perform precise and repeatable welds. In other applications, the EOAT may be a paint nozzle for spray painting surfaces or a glue nozzle for applying a bead of glue with precision and repeatability. The end effector may also be a cutting tool used to remove material from a product that is being worked on. The DaVinci medical robotic system has end effectors that consist of forceps, scissors and scalpels. The Robodoc medical robotic system has an end effector that is a milling burr that is used to mill the bone cuts for knee or hip arthroplasty.

The EOAT may also incorporate various sensors. A collision sensor may be incorporated into the end effector (or other part of the robot) to detect collisions and prevent further damage or even injury. Proximity sensors may also be incorporated to detect when the workpiece or another object is near to the end effector. A force sensor may also be incorporated into the end effector to detect forces and moments.

The end effector described herein may be applied to an industrial robotics system that may be used to perform spinal reconstructive surgery. The end effector may have specific capabilities and features that may allow the robotic system to perform surgical steps more effectively and safely. When the robot is performing surgical steps, the end effector may act as the "hands" of a surgeon. The end effector may hold the instrument. The end effector may maneuver the instrument, like a surgeon would, with precision and the appropriate amount of force. The end effector may also detect problems, like the surgeon's hands would, for example, if too much force is encountered during a surgical step. The end effector may also control the force applied to a cutting tool, which is currently done by "feel" by a surgeon, and adjust the feed rate accordingly. A surgical end effector system that moves the instruments to perform a surgical operation and provide force feedback for safety and control of the instrument motion is described herein.

Figure 1:
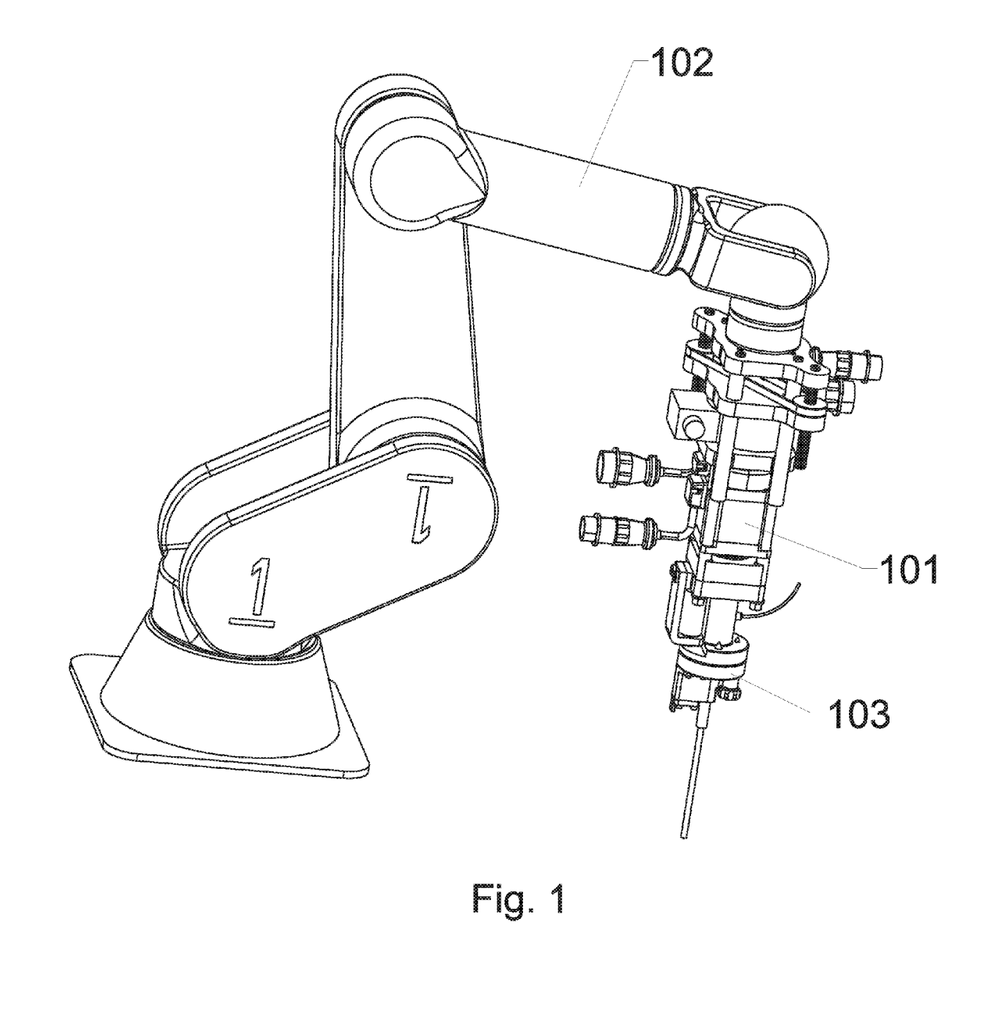
FIG. 1 is an example of a robotic end effector.

FIG. 1 is an example of a robotic end effector. A robotic end effector 101 may be connected to an industrial robot 102. At the end of the end effector 101 may be an instrument holder 103. The robotic end effector 101 may perform many of the functions a surgeon's hand would perform plus some additional unique functions during surgery.

The end effector 101 may be capable of simultaneously performing rotary action, for example, turning a drill, and axial action, for example, pushing a drill, in a very precise way. These motions may be performed by the end effector 101, requiring no movements by the industrial robot 102. The industrial robot 102 may be used to merely position the end effector 101. The rotational and axial position of the tool may be controlled using servo motors. Linear and rotational position encoders may be incorporated internally to the servo motors or externally to the end effector 101 to provide closed loop feedback of linear and rotational position. The rotational position and axial position may also be controlled relative to each other by the servo motor control and the robotic system control. For example, a pedicle tap with a 2 mm pitch on the threads held within the instrument holder of the end effector 101 may be moved axially by 2 mm for every 360-degrees of rotation.

The torsional force and axial force applied by the servomotors may be measured by a multiaxial force transducer. The measured force may be fed back to the control so that the forces applied by the end effector may be well controlled. For example, in the case of a pedicle tap for a pedicle screw, the axial force applied as the instrument is driven into the pedicle may be measured, as is the torsional force required to turn the tap. These force measurements may be used to determine if there is too much force being applied, for example, in the case of a dull instrument, or if too little force is being applied, for example, in the case of poor bone quality. The end effector may also be able to measure a side-load on the instrument. An instrument may not start cutting into bone immediately, but instead skive off to the side, not making the cut in the intended location. Side-load detection may detect this issue and allow for correction. Skiving may happen in manual robot-guided surgery, resulting in undesirable results. Side load measurement may also be desirable when the robotic system is used to perform a milling or burring operation, for example, burring material from the vertebral endplates in preparation for a lumbar interbody fusion, where the robotic system would apply a side load to the cutting tool during the cutting process. The feed rate of a cutting instrument may be optimized using force measurement feedback.

The end effector may be configured to allow an electric current to be passed through it to the end of the instrument being held to allow for neuromonitoring. An electric current may be applied to the clamped end of the instrument. The clamping mechanism of the instrument holder may be insulated to electrically isolate the instrument being held so that the electric current for neuromonitoring does not shunt to the grounded structure of the instrument holder, end effector or industrial robot itself. The robot control system may be able to perform neuromonitoring on a continuous basis while operating to help prevent nerve damage.

Figure 2:
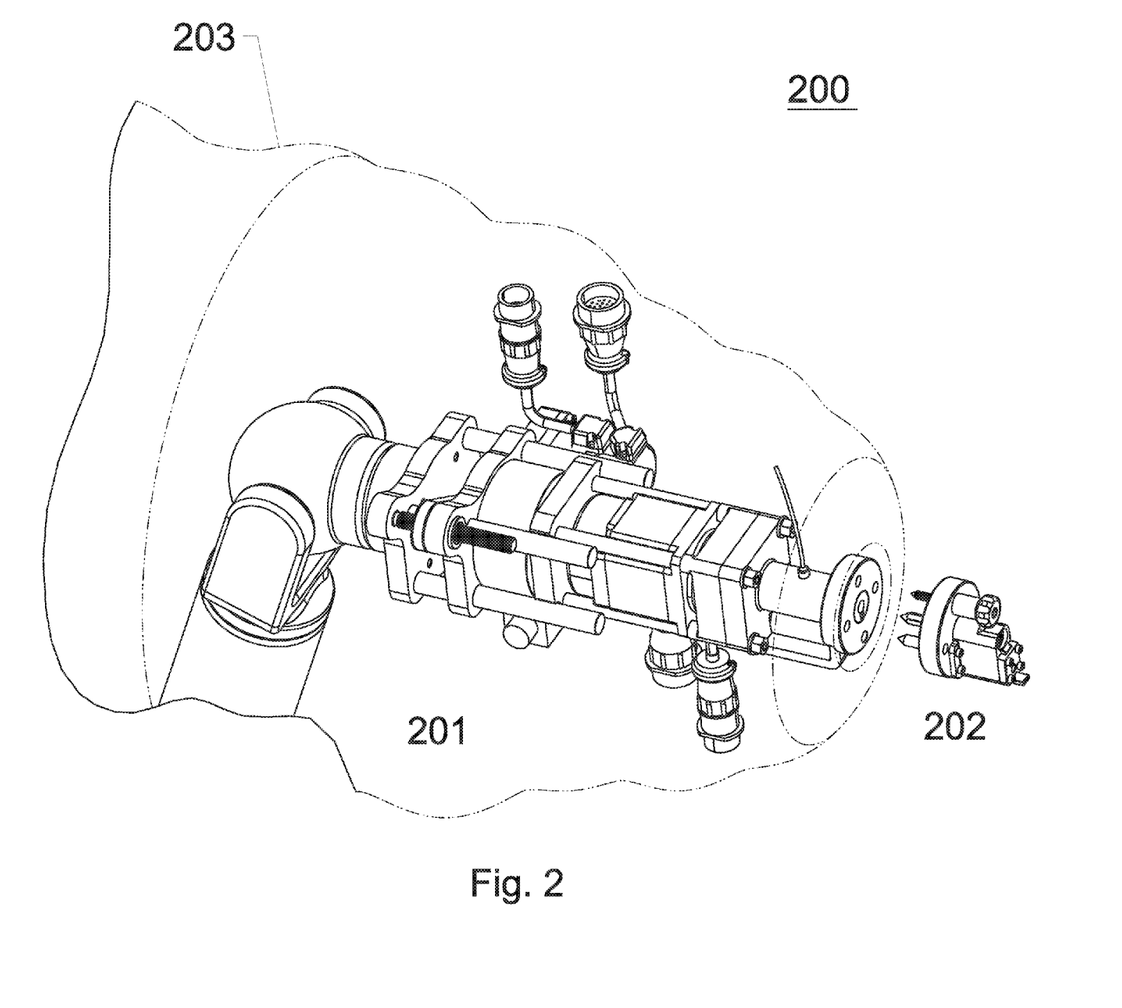
FIG. 2 is an example of the sterile and non-sterile sections of the end effector.

FIG. 2 is an example of the sterile and non-sterile sections of the end effector. The end effector or EOAT 200 may consist of two sections, a sterile section 201 and a non-sterile section 202. The first section 201, the end effector itself, may be non-sterile and covered with a sterile plastic sleeve 203 to prevent contamination of the surgical sterile field. The complexity of the end effector 200 and also the motors and sensors within the device may make sterilization difficult. The industrial robot may also be enclosed in the same sterile plastic sleeve 203. This is the same technique used to cover C-Arm X-ray machines used during surgery. The C-Arm itself is not sterilized but protected with a sleeve. The second section 202, the instrument holder, may be steam sterilized in the same way that surgical instruments are sterilized. The instrument holder may be made from metal and plastic that can withstand sterilization by steam, and may be validated for cleaning and sterilization like any other surgical instrument would be.

The instrument holder may be attached to the end effector with the sterile plastic sleeve in place. The robot may move the end effector into the sterile field where the instrument holder may be attached. The surgical technician may attach the instrument holder to the end effector. The attachment pins for the instrument holder may be pointed to pierce the plastic sleeve when attached to the end effector.

Figure 3:
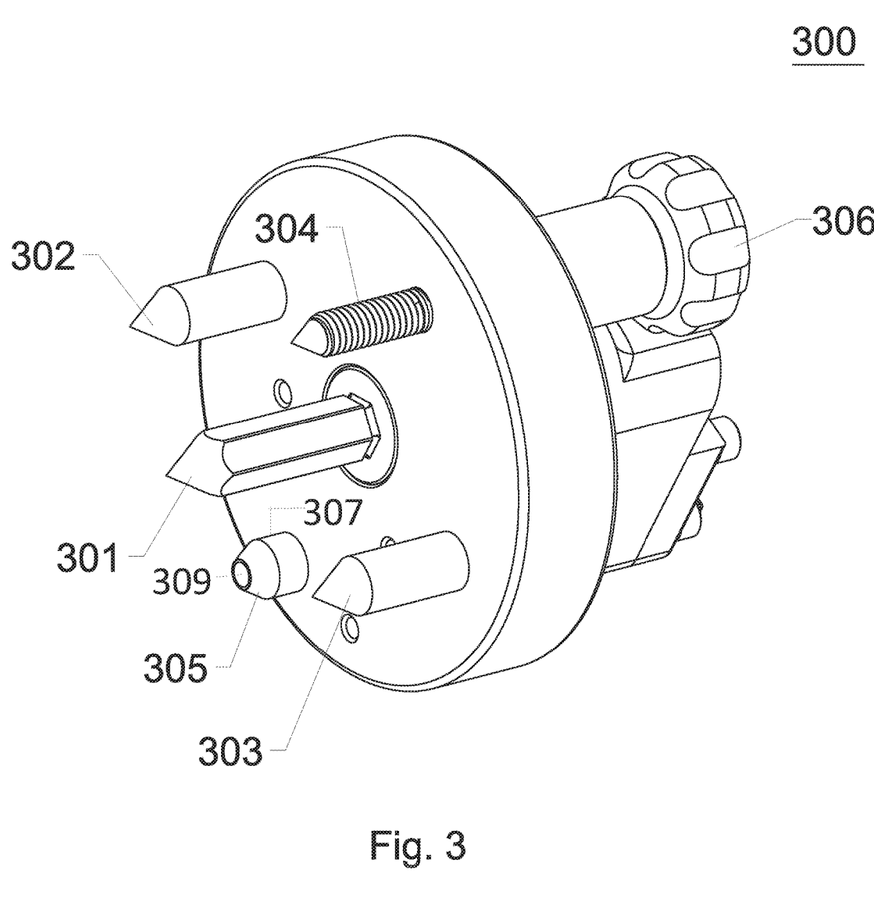
FIG. 3 is an example of a first side of an instrument holder.

FIG. 3 is an example of a first side of an instrument holder. Instrument holder 300 may include five (5) attachment pins. A first pin 301 of the instrument holder may be what passes torque through to the instrument being held. The hexagonal shape mates to a receiving hexagonal shape in the end effector. The first pin 301 may be electrically insulated from the rest of the instrument holder so that a current may be passed through it to the instrument being held and driven for neuromonitoring purposes. Second 302 and Third 303 pins of the instrument holder may be locating pins. These pins 302 and 303 closely fit within receiving holes on the end effector to position the instrument holder in the correct position relative to the end effector. A fourth pin 304 may be a threaded shaft that mates with a threaded receiving hole on the end effector. The fourth pin 304 may be used to securely clamp the instrument holder to the end effector. The knob 306 on the opposite end of the instrument holder may be used to turn the screw. A fifth pin 305 may consist of two parts: an outer sleeve 307 and an inner shaft 309. The outer sleeve may be hollow and tapered at the end to be able to pierce the sterile plastic sleeve. The inner shaft may be free to move axially within the outer sleeve. The inner shaft may be pushed by a linear solenoid 504 (FIG. 5) from within the end effector and sterile plastic sleeve to drive a latch that releases or clamps the instrument being held in the instrument holder.

Figure 4:
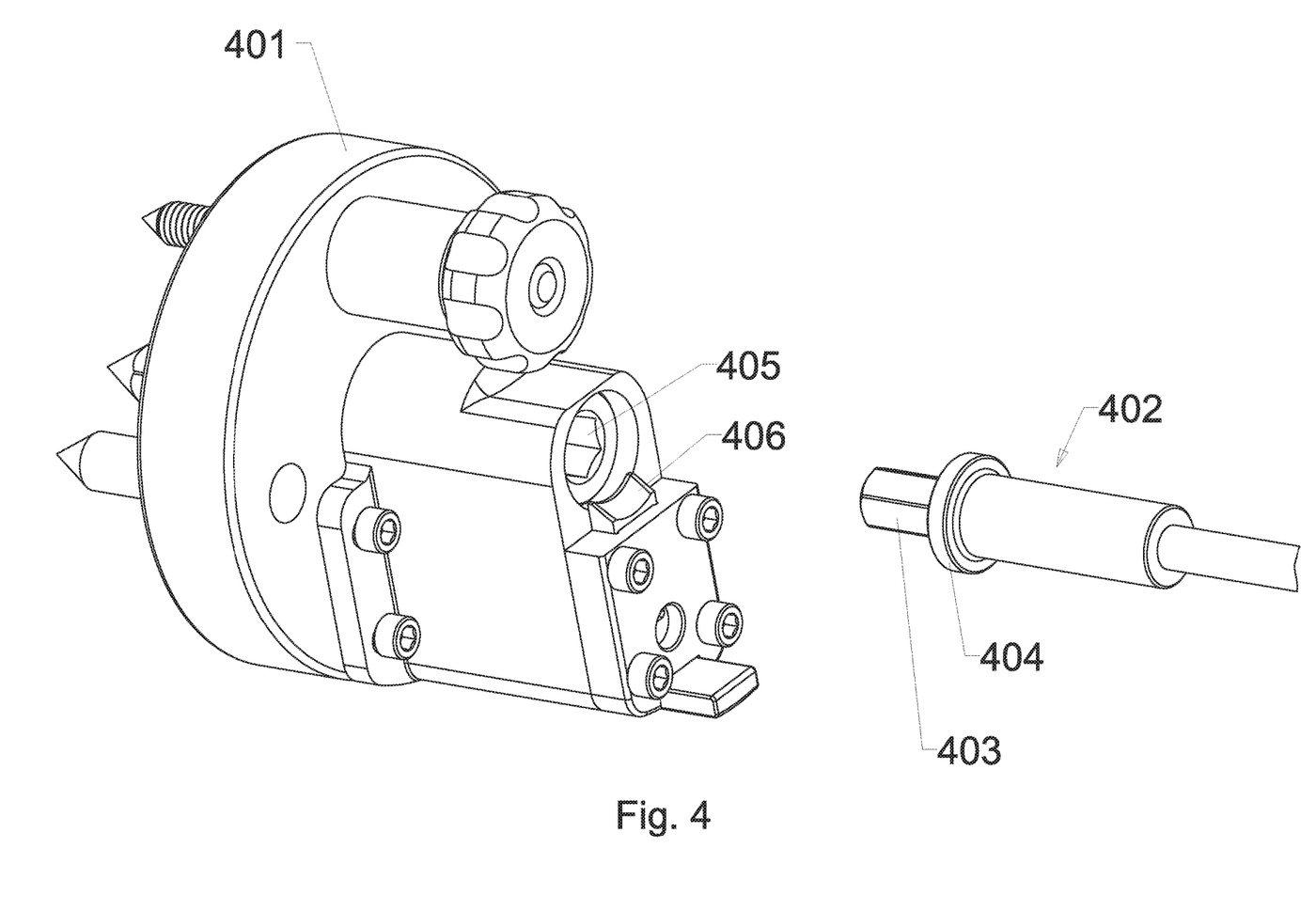
FIG. 4 is an example of a second side of the instrument holder and an instrument for attachment.

FIG. 4 is an example of a second side of the instrument holder and an instrument for attachment. In FIG. 4 an instrument holder 401 and an instrument 402 are shown. Instruments 402 used with the instrument holder 401 may have a hexagonal shape 403 and a collar 404 at the clamped end to mate with the instrument holder 401. The male hexagonal shape 403 on the instrument 402 may be received by the female hexagonal shape 405 on the instrument holder 401. The collar 404 on the instrument 402 may be secured within the instrument holder 401 by a latch 406. The instrument 402 may be inserted into the instrument holder 401 just by pushing it into position, which may be done by a surgical technician or by the robotic system when it "picks up" the instrument from a tool holding rack. The instrument 402 may be released from the instrument holder 401 either by a manual release handle or by the robot, which would energize a solenoid to push the latch 406 to the side. The solenoid may push a tapered wedge that in turn pushes the latch 406 to the side, releasing the instrument 402 from the instrument holder 401.

Figure 5:
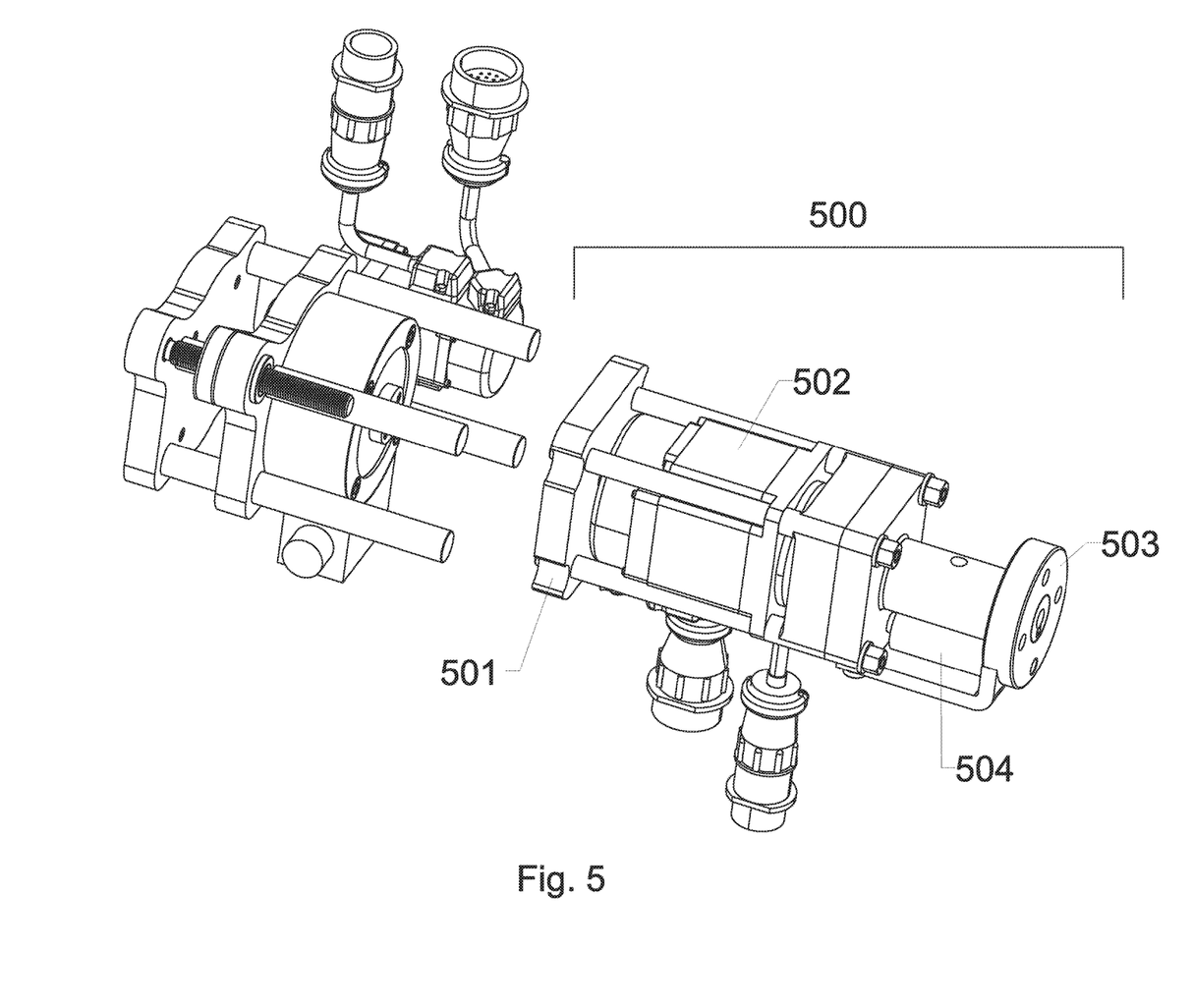
FIG. 5 is an example of a front section of the end effector.

FIG. 5 is an example of a front section of the end effector. The front section 500 of the end-effector may consist of a rigid frame 501 that holds a servomotor 502 (that provides a torsional driving force), a conical bearing (shown in FIG. 6) that protects the servomotor 502 from thrust and side-load, a receiver (shown in further detail in FIG. 6) 503 for the instrument holder, and a solenoid 504 for latching and unlatching an instrument from the instrument holder.

Figure 6:
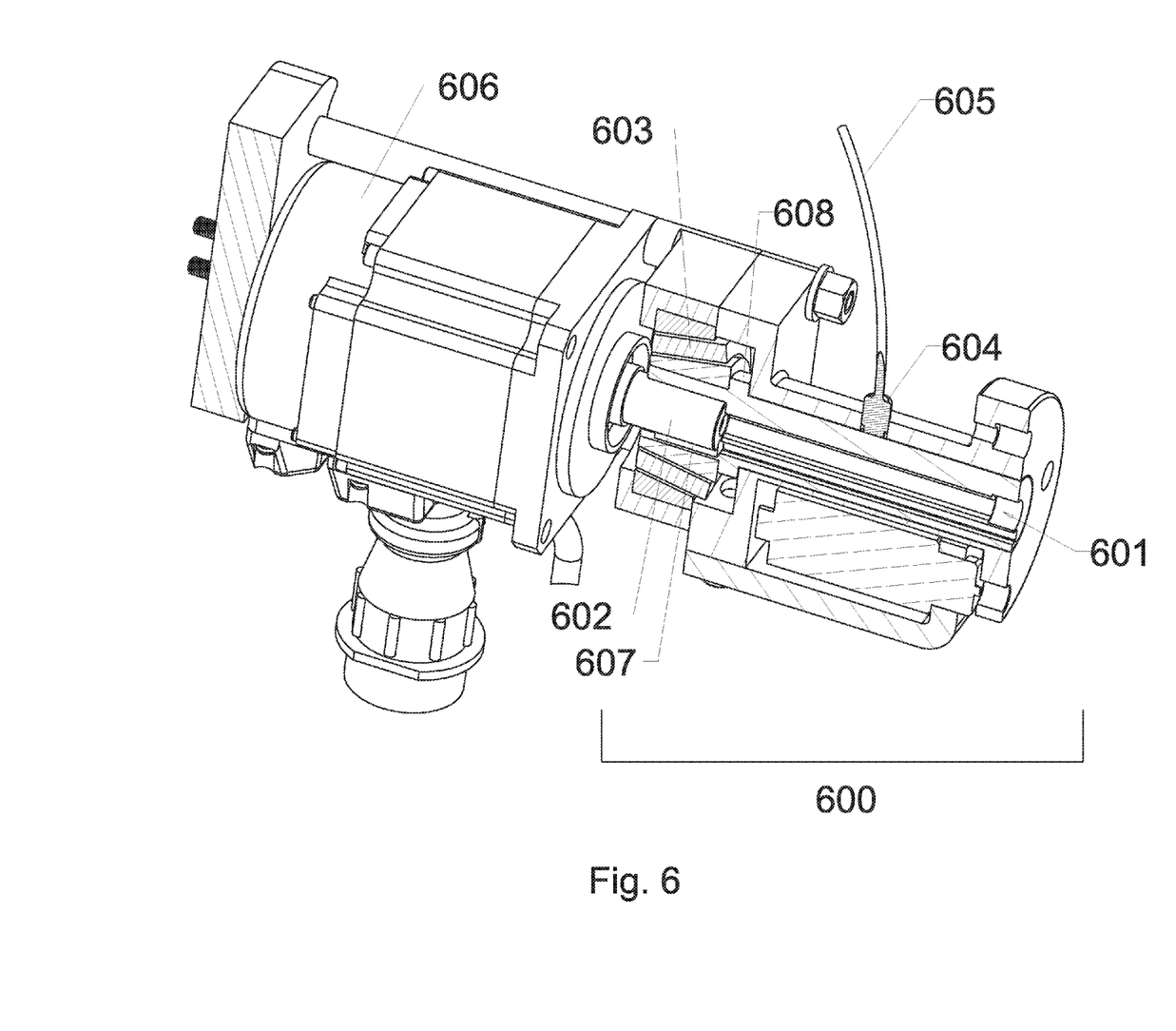
FIG. 6 is an example of inside the receiver for the instrument holder.

FIG. 6 is an example of inside the receiver for the instrument holder. Housed within the receiver 600 for the instrument holder is a driveshaft 601 that transmits torque from the servomotor 606 to the instrument holder. The driveshaft 601 may be connected to the servomotor shaft 602 so that rotational forces may be transmitted from the servomotor 606 to the driveshaft 601; however thrust forces are not transmitted. A key 607 between the servomotor shaft 602 and the driveshaft 601 transmits rotational force only. A collar 608 on the driveshaft 601 may transmit thrust to the conical bearing 603. The thrust and side-load may be transmitted through the conical bearing 603 directly to the front rigid frame of the end effector. The driveshaft 601 may be electrically insulated from the rest of the front rigid frame so that an electric current may pass from the instrument being driven, through the driveshaft 601, to a brush 604 connected to a wire 605 for neuromonitoring.

Figure 7:
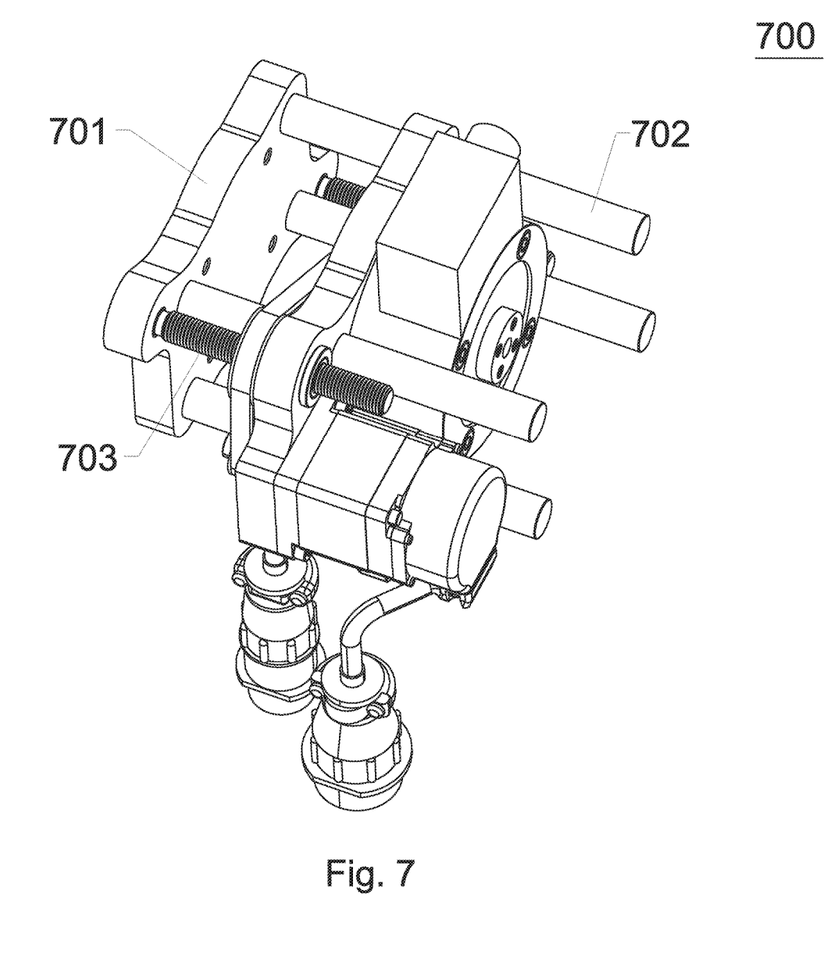
FIG. 7 is an example of a first view of a back section of the end effector.

FIG. 7 is an example of a first view of a back section of the end effector. The back section 700 of the end effector may be rigidly attached to the final segment of the industrial robot arm at a fixed plate 701. This connection may be tailored to fit the connection features of the industrial robot used in the robotic system. One or more smooth shafts 702 and one or more externally threaded shafts 703 may be rigidly attached to the fixed plate 701. These shafts 702 and 703 may be used to guide and move a sliding plate (shown in FIG. 8) and the components attached to it.

Figure 8:
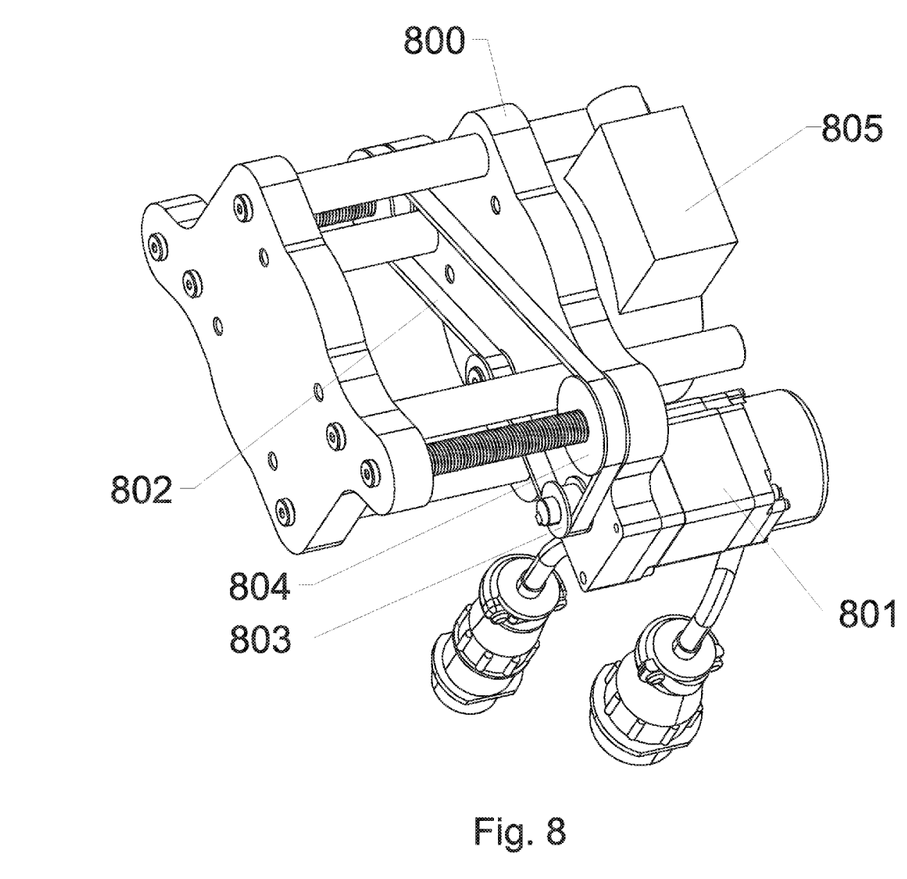
FIG. 8 is an example of a second view of the back section of the end effector.

FIG. 8 is an example of a second view of the back section of the end effector. The sliding plate 800 may move axially along the shafts attached to the fixed plate. A servomotor 801 may be used to drive and control this axial motion. The rotation of the servomotor 801 may be transmitted to one or more internally threaded pulleys or cogs 804 through a timing belt or timing chain 802. A pulley or cog 803 may be rigidly attached to the shaft of the servomotor 801 to drive the timing belt or timing chain 802. The timing belt or timing chain 802 may drive one or more internally threaded pulleys or cogs 804. These internally threaded pulleys or cogs 804 may have teeth to receive the timing belt or timing chain 802 and may be fixed to the sliding plate 800 so that they can rotate about their axis but not move in any other degree of freedom relative to the sliding plate 800. The internally threaded wheels may be threaded onto the externally threaded shafts so that turning them may cause the sliding plate 800 to move relative to the fixed plate as guided by the smooth shafts. The drivetrain may allow the rotational motion of the servomotor 801 to cause axial motion of the sliding plate 800. The servomotor 801 and a controller may control the position, velocity, and acceleration of the sliding plate 800. The servomotor 801 body may be rigidly mounted to the sliding plate 800 so that the shaft of the servomotor 801 may pass through a clearance hole in the sliding plate 800. A multiaxial transducer 805 may also be rigidly mounted to the sliding plate 800.

Figure 9:
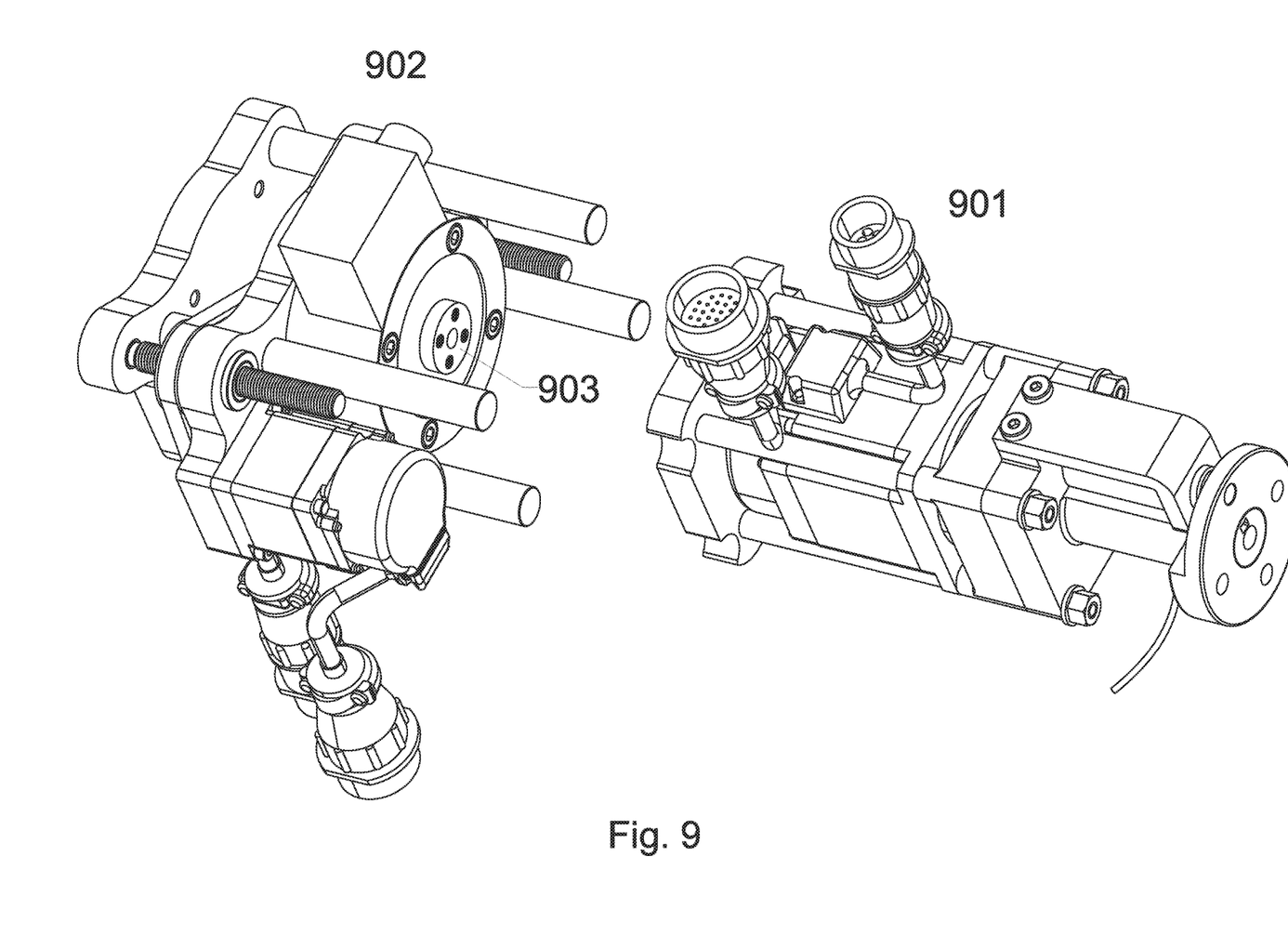
FIG. 9 illustrates the front section and the back section of the end effector being connected.

FIG. 9 illustrates the front section and the back section of the end effector being connected. The front section 901 of the end effector may rigidly attached to the back section 902 of the end effector at a load mounting point 903 of the multiaxial transducer. All degrees of freedom between the front section 901 of the end effector and the back section 902 of the end effector may be constrained by the multiaxial force transducer. With this configuration, all torsional forces, axial forces and side-load forces may be transmitted directly to the multiaxial force transducer.

The programming language of the industrial robot controller may be used to generate a computer code (software) that a robotic surgery system uses to perform surgery. The industrial robot controller and software may coordinate the actions of and feedback from the end effector through a system of electronics designed for this purpose. The end effector described herein may have several electrical inputs and outputs that may be translated to and from inputs and outputs of the industrial robot controller. Part of the end effector system may be a configuration of the electronics for performing this translation.

The inputs and outputs from the electronics on the end effector system may be carried through several different connection types and cable types. Servomotors may typically have one multipin connection for power and one for control and feedback. Transducers may typically use a multi-pin connection. Uni-directional solenoids may typically have one wire to deliver power to energize the device. The neuromonitoring probe may also have a single lead through which current flows when electrical contact is made when a probe gets too close to a neural structure. Cables for all of these connections may be routed from the end effector, along the outside of the robot in a way that does not interfere with its motion, and to the integrated end effector control system. A panel facing the outside of the enclosure for the system may have connectors mounted to it so the appropriate cables from the end effector may be plugged in to the integrated end effector control system.

The inputs and outputs from the industrial robot system controller may also be delivered to the integrated end effector control system using the appropriate cables. Connectors may be mounted to a second panel on the end effector control system enclosure so that the cables from the industrial robot controller may be plugged into the end effector.

Different connectors for different inputs and outputs may be used on the robot system and end effector connection panels to help ensure that everything is connected correctly when the system is being installed by a user.

The enclosure for the integrated end effector control system may contain all of the required electronics to translate the inputs and outputs from the end effector system. The system may require an independent power supply which may be mounted inside of the enclosure and connected to standard AC current available in an operating room. The power supply may be an uninterruptable power supply (UPS) system to prevent damage to the end effector system or electronics in the case of a power interruption. A cooling system may also be incorporated to keep the electronics from overheating.

The servomotor controller electronics may be a subsystem of the integrated end effector control system. The servomotor controller electronics may be an off-the shelf component mounted within the enclosure. The servomotor controller electronics may receive power from the UPS mounted within the enclosure. The connections for the two servomotors in the end effector may be wired from the servomotor controller electronics to the end effector connection panel. The inputs/output from the servomotor controller electronics, which connect back to the robot control computer system, may be wired to the robot system connection panel. The connections from the servomotor controller electronics to the robot control computer system may be standard since many servomotor controllers are designed to be integrated into industrial automation systems.

The interface module for the multiaxial transducer may also be a sub-system of the integrated end effector control system. The interface module may be an off-the shelf component mounted within the enclosure. The interface module may receive power from the internally mounted UPS also. The input and output from the transducer may come from the end effector control panel. The output to the robot system controller computer may go out through the robot control connection panel.

The neuromonitoring electronics module may be a subsystem of the integrated end effector control system. The module may provide stimulating current for the neuromonitoring and detect current passed from the end of the instrument through the patient to the neuromonitoring skin pad. This signal may be conditioned and transmitted to the robot system controller computer. Power for the neuromonitoring electronics module may be provided by the internally mounted UPS.

The solenoid signal converter may relay a binary signal transmitted from the robot system controller computer to either open the latch to release the clamped instrument or allow the latch to return to the closed position to clamp the instrument. The solenoid signal converter may generate a current to energize the latch releasing solenoid when the binary signal is received. This may be necessary since voltage and current from the binary signal may not be enough to energize the solenoid.

Figure 10:
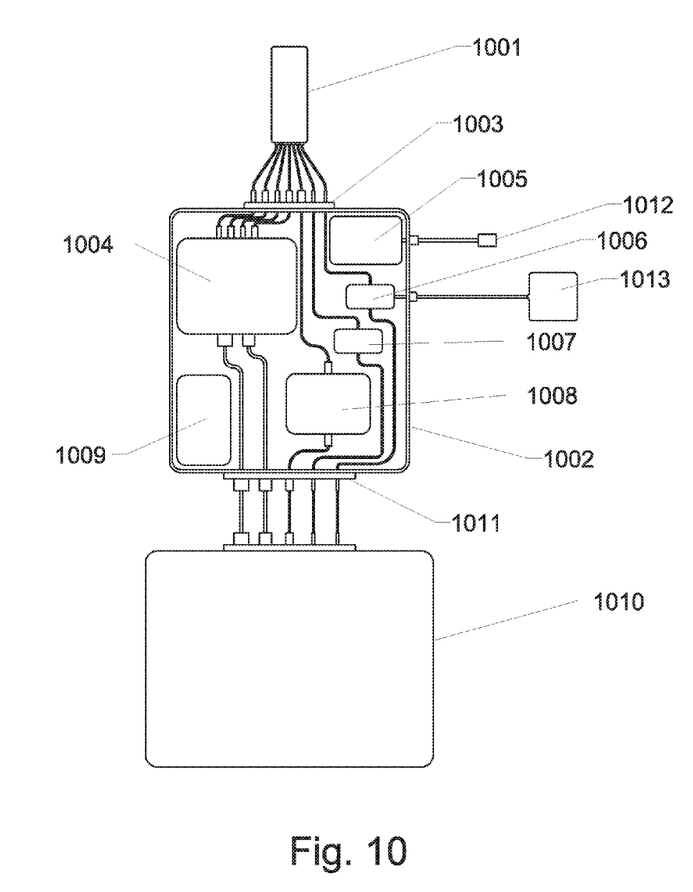
FIG. 10 is an example of an integrated end effector control system interfacing with the end effector and the industrial robotics system.

FIG. 10 is an example of an integrated end effector control system interfacing with the end effector and the industrial robotics system. The end effector 1001 may be connected to the integrated end effector control system enclosure 1002 via an end effector connection panel 1003. The integrated end effector control system enclosure 1002 may include a solenoid motor controller module 1004, a UPS 1005, a neuromonitoring electronics module 1006, a solenoid signal converter 1007, a transducer interface 1008, and a cooling system 1009. The integrated end effector control system is connected to the robot system controller computer 1010 via a robot control connection panel 1011. The UPS 1005 may be connected to the AC power 1012. The neuromonitoring electronics module 1006 may be connected to a neuromonitoring skin pad 1013.

Many different tools may be attached to the instrument holder. For example, some of the tools used may be a wire inserter, a tap, a headless screwdriver, a tulip popper, a cap inserter, a cap torque driver/counter torque, a vision system (for example, a camera) and the like. Additionally, the end effector may be capable of reading an RF signal from a smart implant.

K-wire management may be described herein. The K-wire management may include a nitinol wire that is deployed in a spiral helix shape. The K-wire may be forced to a straight shape within an internal cannula. A K-wire may also be pre-loaded into a headless cannulated screw driver. The K-wire may be put into place with the use of two robots. The first robot may include the use of the end effector described herein. The first robot holds the K-wire while the second robot uses a K-wire gripper to hold the K-wire in a fixed position.

After K-wire insertion, the wire may be held in a fixed position relative to the vertebral body, with the end effector moving pedicle preparation tools axially along the wire. The end effector wire holder and K-wire are designed to prevent the wire from being "pushed along" with the pedicle preparation tool. In contrast, 'pushing along" wire may cause the wire to penetrate too far, potentially resulting in serious injury for a patient.

For a cap inserter tool, two robots may be used. The first robot may include the end effector described herein. The first robot uses the cap inserter tool to insert the cap into a previously placed pedicle screw tulip, while the second robot bends and inserts a rod through the inserted tulip and cap. The first robot may then use the cap inserter tool to tighten the cap, locking the rod into the pedicle screw tulip.

For the headless screwdriver tool, the screw a simply snaps-on and locks in place for insertion. A guide wire may already be preloaded along with a pedicle screw. The guide wire may be a NITINOL material. The guide wire may be loaded into a headless screw driver straitened (under tension). However, once the guide wire is deployed, the end relaxed into a pigtail or helical spiral shape.

A dynamometer may be inserted between the headless screwdriver and the power drill to measure the (maximum) torque applied when inserting the screw. The dynamometer may also be used to limit the amount of torque applied for safety reasons. Torque may also be measured using the load (amps) drawn by the drill motor. A shunt may be placed between the battery and the power drill with resistance that provides for a standard 4-20 mA current as measure across the shunt. A data acquisition device and software may be used to record data and calibrate from current (mA) to torque (Nm).

The end effector may be capable of driving a screw by itself using an automatic screwdriver. For an automatic screwdriver, a stepper motor may count revolutions once the screwdriver begins driving. A screw may be driven in very controlled increments. Data from the recorded torque aids in sizing a motor required for the automatic screwdriver.

A head popper may be used to insert a tulip onto a screw, to guide a rod into place, for verifying the seating of a rod, assembling a locking cap, removing a locking cap, and the like.

A vision system may verify hardware, for example, length, diameter, size, and the like. The vision system may be used for positioning and alignment of implants and the like. The vision system may be part of the industrial robot control package or a standalone system. The vision system may include shape recognition software.

In an exemplary embodiment according to the present invention, data may be provided to the system, stored by the system and provided by the system to users of the system across local area networks (LANs) (e.g., office networks, home networks) or wide area networks (WANs) (e.g., the Internet). In accordance with the previous embodiment, the system may be comprised of numerous servers communicatively connected across one or more LANs and/or WANs. One of ordinary skill in the art would appreciate that there are numerous manners in which the system could be configured and embodiments of the present invention are contemplated for use with any configuration.

In general, the system and methods provided herein may be consumed by a user of a computing device whether connected to a network or not. According to an embodiment of the present invention, some of the applications of the present invention may not be accessible when not connected to a network; however a user may be able to compose data offline that will be consumed by the system when the user is later connected to a network.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

The invention claimed is:

1. An end effector system for use in spinal surgery, the end effector comprising:
   a sterile section, the sterile section comprising an instrument holder having:
      a latch releasably retaining an instrument for performing spinal surgery, and
      pins having tapered tips for piercing a plastic sleeve, one of the pins having a hollow outer sleeve and an inner shaft axially moveable relative to the outer sleeve to move the latch between a released position and a clamped position; and
   a non-sterile section, the non-sterile section comprising an end effector having:
      a motor, wherein the motor applies a torsional and axial force to the instrument.

2. The end effector system of claim 1, wherein the end effector simultaneously performs a rotary motion and an axial motion.

3. The end effector system of claim 1, wherein non-sterile section is covered with a sterile plastic sleeve.

4. The end effector system of claim 1, wherein instrument holder has five pins.

5. The end effector system of claim 4, wherein a first pin is used to pass torque through to an instrument.

6. The end effector system of claim 4, wherein a second pin and a third pin are locating pins.

7. The end effector system of claim 4, wherein a fourth pin is a threaded shaft that mates with a threaded receiving hole of the end effector.

8. The end effector system of claim 1, wherein the end effector is connected to a robot controller.

9. The end effector system of claim 1, wherein a K-wire or wire inserter is attached to the instrument holder.

10. The end effector system of claim 1, wherein a vision system is attached to the instrument holder or end effector.

11. The end effector system of claim 1, wherein the motor comprises a first motor that applies a torsional force to the instrument, and a second motor that applies an axial force to the instrument.

12. The end effector system of claim 1, wherein one of the pins has a predetermined geometric shape rotatable within the instrument holder, and wherein the instrument holder further includes a bushing connected to the predetermined geometric shape pin, and wherein the bushing includes a female end for receiving a tool and is rigidly connected to the predetermined geometric shape pin.

13. The end effector system of claim 1, wherein the instrument includes:
   a first pin to receive torque from the instrument holder and is electrically insulated for neuromonitoring, and
   a shunt for shunting, wherein the shunt provides about 4-20 mA current for shunting.

14. The end effector system of claim 11, further comprising:
   a fixed plate for attaching the end effector to a robot arm, and a sliding plate moveable relative to the fixed plate; and
   a pulley attached to a shaft of the second motor, the pulley being operable to drive a timing belt that drives internally threaded pulleys that are threaded onto externally threaded shafts connected to the sliding plate to cause the sliding plate and the instrument to move axially relative to the fixed plate.

15. The end effector system of claim 1, wherein the instrument holder further comprises a solenoid operable to move the latch between an open position and a closed position.

16. The end effector system of claim 1, wherein the instrument holder further comprises a receiving recess for receiving the instrument, and wherein the latch is adjacent to an opening of the receiving recess to prevent axial movement of the instrument therein.

17. An end effector system for a robotic surgery system comprising:
   a non-sterile section that includes an end effector having:
      a motor for applying torsional and axial forces to an instrument; and
   a sterile section that includes an instrument holder having:

a pin having a non-cylindrical geometric shape rotatable within the instrument holder, and a bushing connected to the pin, wherein the bushing includes a female end for receiving a tool.

18. The end effector system of claim 17, wherein the pin is rigidly connected to the bushing and rotatable within the instrument holder.

19. An end effector system for a robotic surgery system comprising:

an end effector;

an instrument holder connected to the end effector; and an instrument having:

a first pin to receive torque from the instrument holder, wherein the first pin is electrically insulated for neuromonitoring, and a shunt for shunting.

20. The end effector system of claim 19, wherein the shunt provides about 4-20 mA current for shunting, and wherein the instrument holder includes a driveshaft, a brush adjacent the driveshaft, and a wire connected to the brush for neuromonitoring.

\* \* \* \* \*